United States Patent [19]
Komarek

[11] Patent Number: 5,370,007
[45] Date of Patent: Dec. 6, 1994

[54] FIBER ANALYSIS SYSTEM

[76] Inventor: Andrew R. Komarek, 172 N. Main St., Fairport, N.Y. 14450

[21] Appl. No.: 75,664

[22] Filed: Jun. 11, 1993

[51] Int. Cl.$^5$ .......................... G01N 33/02; G01N 5/04
[52] U.S. Cl. ........................................................ 73/866
[58] Field of Search .................... 73/866; 162/49, 198, 162/263

[56] References Cited

U.S. PATENT DOCUMENTS

| | | | |
|---|---|---|---|
| 4,657,767 | 4/1987 | Meade | 426/471 |
| 5,219,601 | 6/1993 | Devic | 426/254 |

FOREIGN PATENT DOCUMENTS

| | | | |
|---|---|---|---|
| 1401663 | 7/1975 | United Kingdom | 73/866 |

OTHER PUBLICATIONS

Critical Conditions in Determining Detergent Fibers, D. R. Mertens, USDA—Agricultural Research Service, U.S. Dairy Forage Research Center, Madison, Wis. 53706.
Feed Industry Red Book 1992 Edition, Analyses of Fee Ingredients, Ruminants, Dr. D. L. Preston of Lubbock, Texas.
Forage Fiber Analyses (Apparatus, Reagents, Procedures, and Some Agricultural Research Service—United States Department of Agriculture, Agriculture Handbook No. 379, H. K. Goering, research dairy husbandman, and P. J. Van Soest, formerly chemist, Animal Science Research Division, Agricultural Research Service.

Primary Examiner—Hezron E. Williams
Assistant Examiner—Daniel S. Larkin
Attorney, Agent, or Firm—Harris Beach & Wilcox

[57] ABSTRACT

A method of fiber analysis for feedstuffs and foods which comprises providing a sample of feedstuff or food of a predetermined weight in a sealed fabric bag having a porosity selected to allow for the removal of the solubilized components of the sample by solubilizng them in the detergent from the bag while retaining the fiber components of the sample within the bag; the bag is placed in a heated detergent solution for a time sufficient to solubilize the non-fiber components of the sample while retaining the fiber components within the bag. The bag is then rinsed in an aqueous solution to remove residual detergent, followed by rinsing in an organic solvent and drying and then weighing the bag to determine the fiber content. The bag containing the sample is also disclosed.

9 Claims, 4 Drawing Sheets

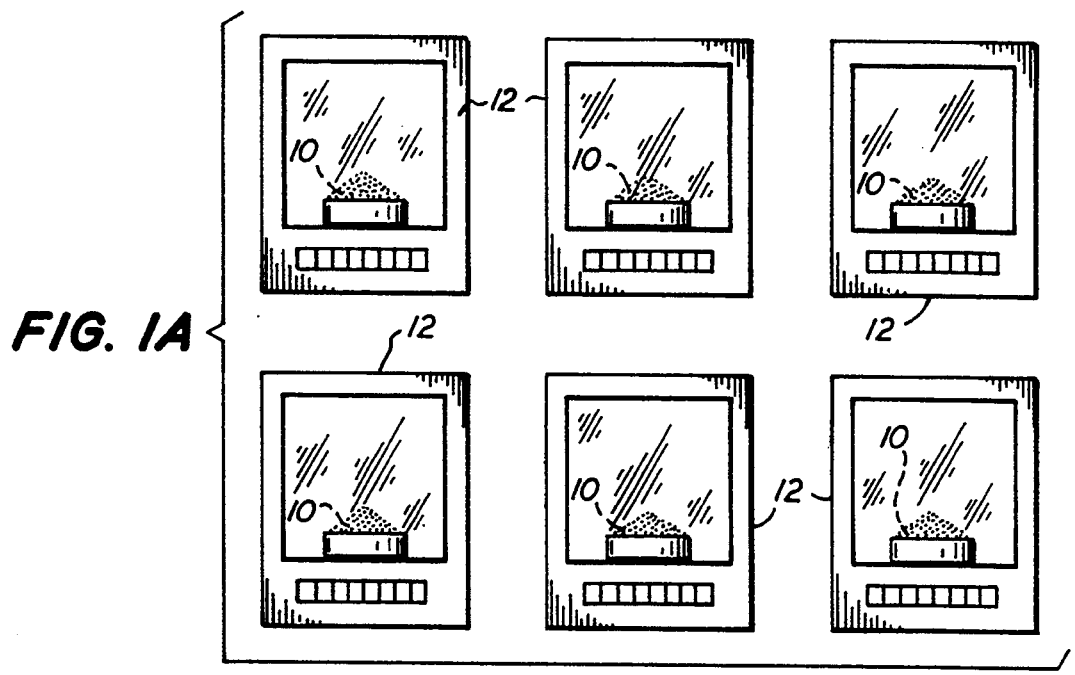
FIG. IA
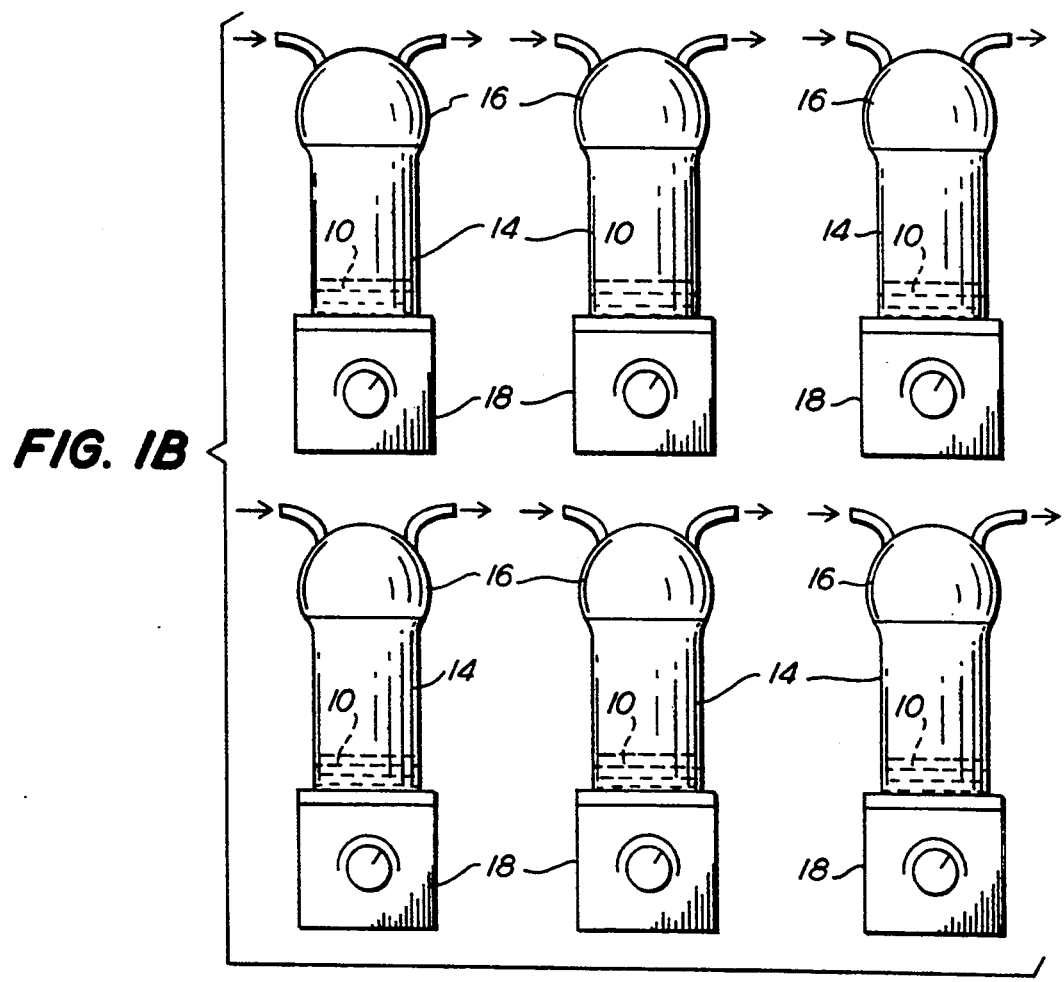
FIG. IB

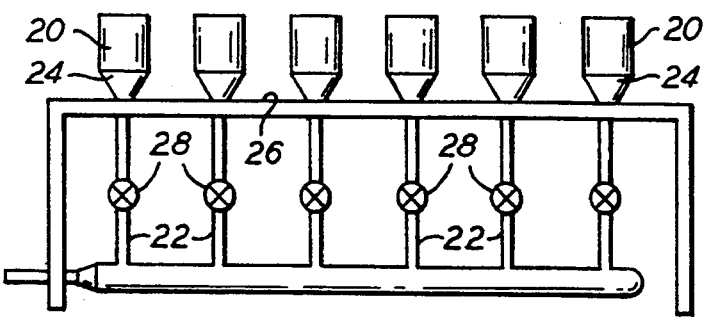
FIG. IC
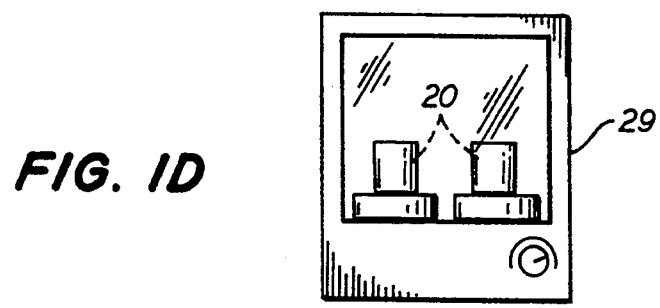
FIG. ID
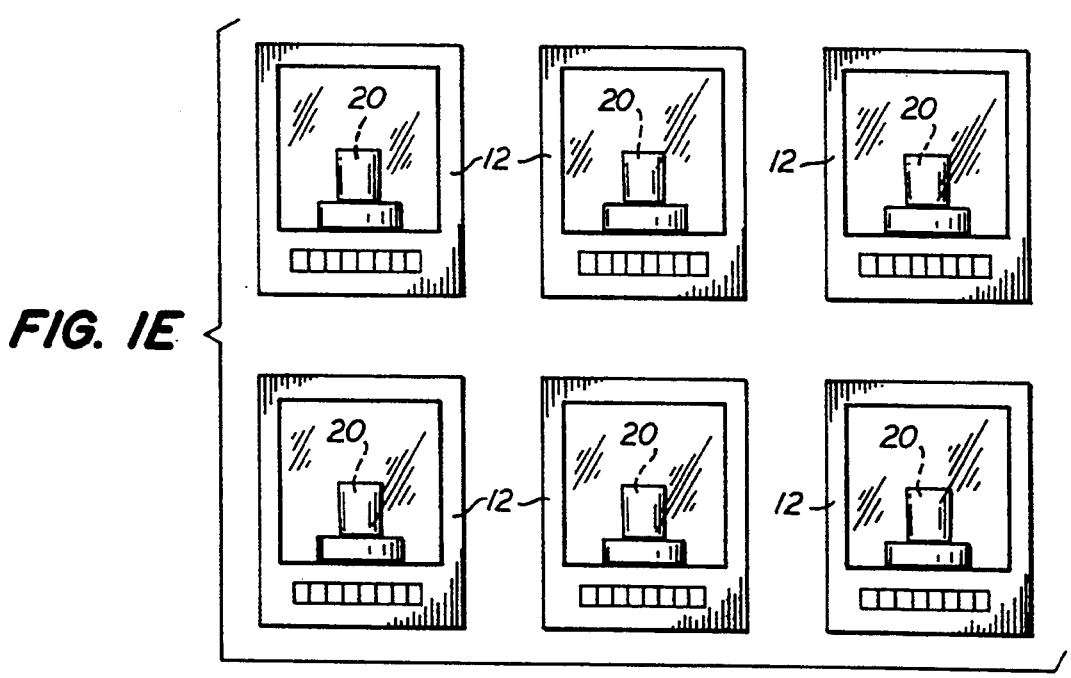
FIG. IE

FIBER ANALYSIS SYSTEM

BACKGROUND OF THE INVENTION

The invention relates in general to fiber analysis, and more specifically to an improved fiber analysis system which exhibits improved efficiency in labor and time, and minimizes the amount of apparatus required.

In general, fiber analysis is conducted in order to determine analytical data that will aid in predicting the extent of the nutritional availability of forage and other feedstuff for animals. Fiber determinations are also important in human nutrition, and have gained increased prominence since the benefit that fiber has on the gastrointestinal tract has been recognized.

The currently accepted techniques used for fiber analysis include neutral detergent fiber (NDF) analysis and acid detergent fiber (ADF) analysis originally described by P. J. Van Soest and others and involves the solubilization of non-fiber components of the feed in boiling detergent solution, with the residual material described as neutral detergent fiber or acid detergent fiber depending on the solution used. In this procedure, the recovery of the residual fiber by filtering and subsequent washing, utilizes individual glass crucibles and filtration units. The filtration procedure associated with the analysis requires pains taking, labor intensive and time consuming tasks. Although improvements in the filtering procedures have been made they still require individual handling and filtering which limits the efficiency of these procedures.

Agricultural Handbook No. 379 entitled *Forage Fiber Analyses (Apparatus, Reagents, Procedures, and Some Applications)*; pages 1–20; by H. K. Goering and P. J. Van Soest; Agricultural Research Service of the United States Department of Agriculture describes in detail these currently available procedures which are the standard for government, industry, and academia. The criteria set forth in the article describes the equipment and labor intensive requirement of the procedure in which typically a minimum of six (6) detergent reflux containers and attendant heating apparatus are required to maintain boiling solutions that keep the fiber in continuous suspension. Similarly, a minimum of six (6) filtration units are also required to accommodate individual products from each of the reflux containers. It is stated in the article that the standardized methods and equipment in the laboratory are mandatory in order to obtain precise analytical results. It is recommended in the article that enough equipment be provided to adequately run a basic analysis such as cell wall (neutral detergent fiber) continuously for an eight hour period at a recommended 12 unit refluxing apparatus and a drying oven large enough to hold 80 crucibles to make this objective possible.

It can therefore be seen from the above, that the current state of the art with regard to fiber analysis requires a significant expenditure and commitment to laboratory equipment associated with a difficult labor intensive and time consuming procedure which is inherent in the current standard procedure for fiber analysis.

There is, and has been a continuing need in this field for a procedure that will significantly improve the efficiency of the fiber analysis process that minimizes the investment in equipment, and yet insures that the analysis is equivalent to the standard procedure with regard to the eventual determination of fiber content.

SUMMARY OF THE INVENTION

The present invention relates to the discovery that a new procedure utilizing a bag as a filter may be employed in place of the standard NDF or ADF procedure described above. The time consuming, equipment intensive filtering method of the prior art has been replaced in the present invention by a fabric filter bag of a predetermined porosity. In this procedure a sample of feedstuff of a predetermined weight is placed in an individual fabric bag and sealed closed. In the interest of economy and efficiency, a plurality of bags are usually preferably processed at the same time. The bags are placed in a container of heated detergent solution for a time sufficient to remove all of the soluble solids from the feedstuff while retaining the fiber components of the feedstuff within the bag. The bags are then removed from the detergent container and rinsed in a hot water wash to remove any residual detergent from the solution. The bags are then cleaned with a final organic solvent rinse, dried and then weighed to determine the fiber content of the feedstuff. The process of the present invention provides data which is in excellent agreement with NDF and ADF values with comparable precision.

BRIEF DESCRIPTION OF THE DRAWINGS

FIGS. 1A–1E represents a schematic illustration of the Association of Official Animal Chemistry (AOAC) approved method of fiber analysis currently used in the field.

DETAILED DESCRIPTION OF THE INVENTION

Figure 2A:
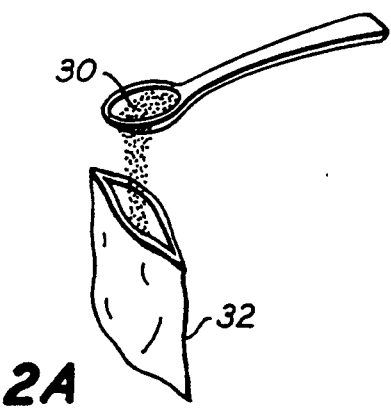
FIGS. 2A–2E represent a schematic illustration of the fiber analysis technique of the present invention.

FIGS. 1A–1E schematically illustrates the standard prior art fiber analysis technique currently used by the government, industry, and academia. In the FIG. 1A, six samples 10 are individually weighed on any suitable laboratory scale or balance 12 and comprise between 0.5 to 1.0 gram samples of an appropriate feedstuff. The samples are typically contained on a weighing dish (not shown). The samples are measured to 0.0001 gram accuracy. The samples 10 are then placed individually (FIG. 1B) in 600 ml berzelius beakers 14 without a spout, which are closed with a reflux top 16, and supported at their base by a hot plate 18 which heats the appropriate neutral detergent or acid detergent solution depending upon the fiber analysis process being used. A 100 ml solution is contained in each individual berzelius beaker, and with the sample placed in the solution, the beaker is brought to a boil and maintained at a low boil for approximately 60 minutes during which substantially all of the nutrients are soluablized in the detergent solution. The fiber content remains unsoluabilized and is evidenced as discrete particles which remain suspended in the solution. Following this operation, the contents of each individual beaker are then poured into a 50 ml capacity pre-tarred Gooch-type pyrex flitted glass crucible 20, coarse porosity (FIG. 1C). A vacuum system 22 is placed at the bottom of the Gooch crucible, and as the solution is poured through the fritted glass 24, the solution is sucked by vacuum out of the system and out of the Gooch crucible while the discrete fiber particles, which are not in solution, are trapped in the fritted glass filter. The crucible is rinsed several times with a hot water wash in order to remove all the detergent from the fiber particles followed by a solvent acetone rinse to completely clean the crucible and remove all extraneous materials from the fiber particles. The crucibles are maintained in place on a fixture 26. Valves 28 are positioned below each individual crucible in order to control the vacuum. Each of the individual samples is then dried in an oven 29 at 90°–95° C. (FIG. 1D) while contained in the Gooch crucible and the crucible is then weighed (FIG. 1E) in order to determine the fiber content of each individual specimen. This procedure, both for acid or neutral detergent fiber analysis is a standard procedure currently used in the art, and is more fully described in the Forage Fiber Analyses article by Goering and Van Soest referred to above, which is incorporated herein by reference.

In the present invention, as illustrated in FIGS. 2A–2E of the drawings, up to twenty-four (24) samples 30 were separately weighed (not shown) and placed individually in a porous fabric bag 32 such as a polyester, or the like, and heat sealed by heat sealer 34 in order to properly close the bag. The 24 bags were then placed in a stainless steel bag suspender which was then placed in a heating apparatus 60 (FIG. 2D and FIG. 3) containing a heated detergent solution.

Figure 2B:
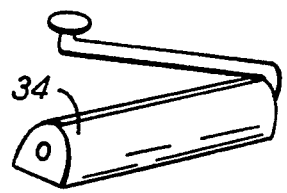
Figure 2C:
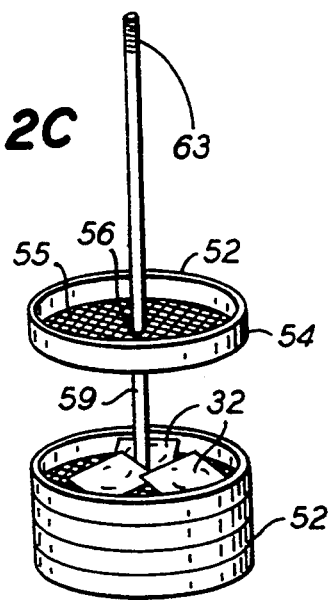

As shown in FIG. 2C, the bag suspender 50 is made of stainless steel and in the form of a plurality of metallic disks 52 in the form of an outer circumferential member defining a ring 54 and an internal perforated metallic porous center section 55 having a center hole or bore 56 sized to accommodate support rod 59. A plurality of disks 52 are supported, one over the other, on rod 59 with a plurality of bags supported on each disk 52 in order to fix them in place during exposure to the heated detergent solution. The rod 59 has an enlarged section 61 (FIG. 3) at its lower end to stop and hold the first disk in place at the bottom of the rod and a threaded section 63 at its upper end to allow it to be threaded into a movable coupling 79, with the lower end of the bag suspender 50 being held in place within internal chamber 67 of heating apparatus 60.

Figure 2D:
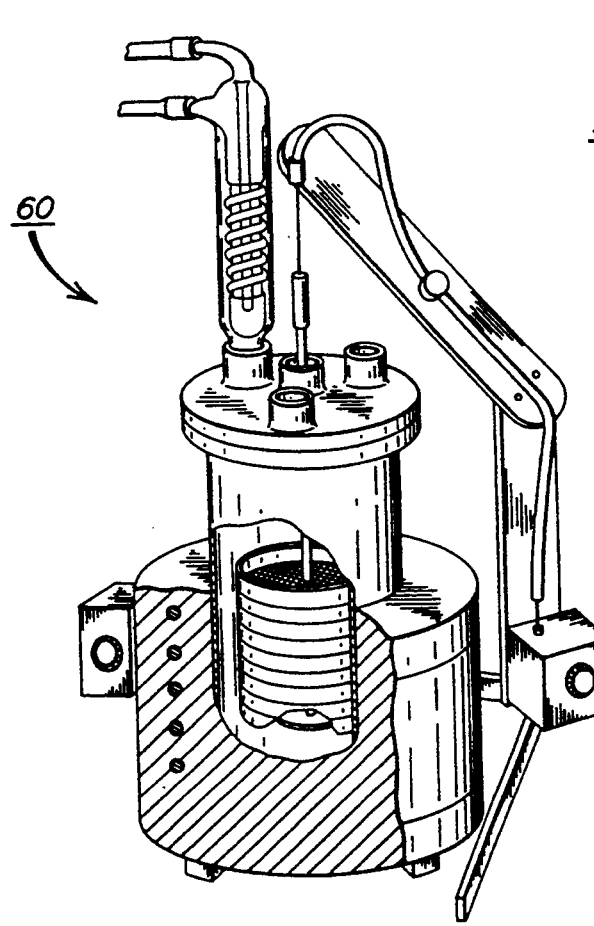
Figure 2E:
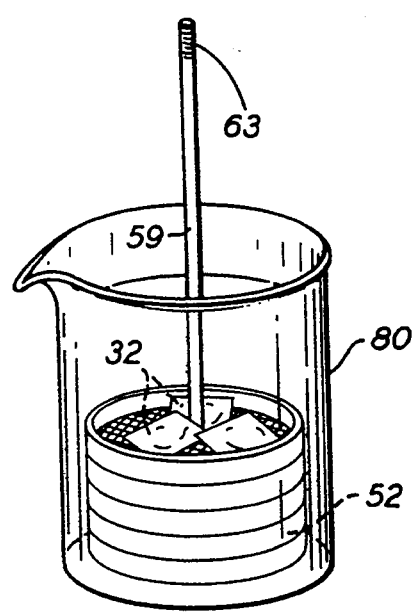
Figure 3:
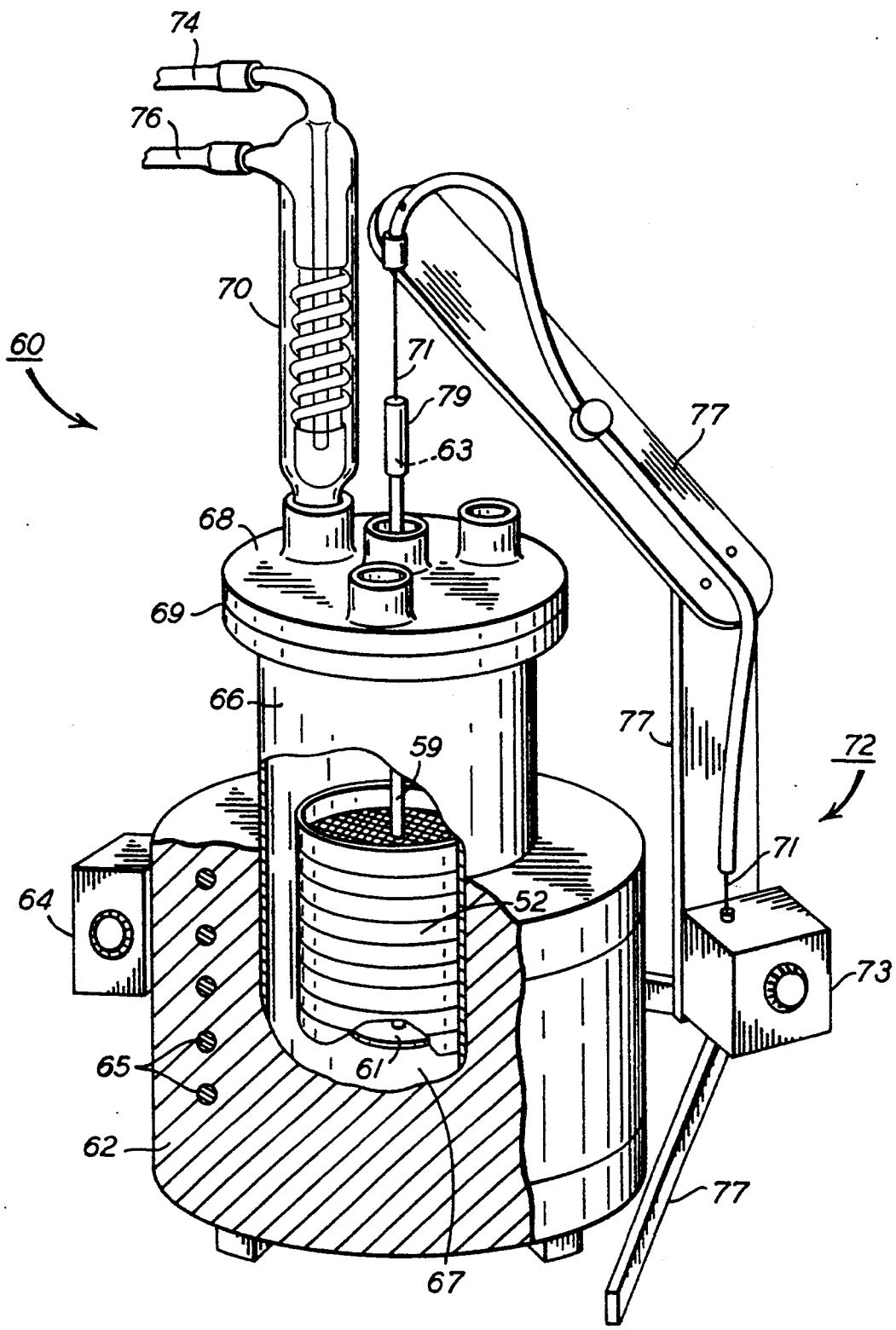
FIG. 3 is an enlarged perspective view of FIG. 2D with a partial sectional view, of suitable apparatus for use in carrying out the present invention.

FIG. 3 is an enlarged view of FIG. 2D and illustrates apparatus 60 suitable for use in carrying out the present invention. The apparatus comprises a heating mantle 62 having a mantle heating controller 64 which actuates and controls a series of heating coils 65 which heats internal chamber 67 which contains the detergent solution. In the present invention the bags are preferably heated in the detergent solution just below the boiling temperature of the solution. A temperature of about 97°–99° C. has been found to be suitable. The detergent solubilization can be carried out at or above the boiling temperature of the solution, but in some instances the phase change from the liquid to the vapor can cause an unwanted ballooning of bags, and adversely effects the solubilization mechanism. The heating mantel 62 contains a reaction kettle 66 which defines an internal chamber 67, and further contains a kettle top 68 and a condenser 70 which contains a water inlet 74 and water outlet 76 for cooling the condenser. Access to internal chamber 67 is accomplished by removing kettle top 68 from the reaction kettle 66 at interface 69. Typically the reaction kettle and kettle top may be held together by external mechanical clamping means (not shown). Agitator mechanism 72 controlled by control switch 73 which moves wire 71 is provided to move coupling 79 holding rod 59 of the bag suspender in an up and down motion during the detergent heating operation in order to enhance the solubility. The wire 71 is supported by a bracket assembly 77 which also supports switch 73. Exposure to the heated detergent solution results in the solubilization of all soluble solids from the feedstuff, and results in the fiber being left in the bag.

If the solution boils and changes phase the vapor is condensed by the condenser and drips back into the kettle. The purpose of the condenser is to maintain consistent solution concentration.

Any heating apparatus which will accomplish the objectives of the invention can be used. Suitable apparatus for carrying out the detergent heating step of the present invention is available from Ankom Company of Fairport, NY under the tradename No. 1 Fiber Equipment Package. Following the solubilization in the detergent in chamber 67, the bags in the bag suspender are then removed from the chamber and immersed ha a hot water wash in container 80 (FIG. 2E) in order to remove any residual detergent solution remaining on or in the bags. The bags are then placed in an organic solvent wash container (not shown) such as acetone, followed by drying in an oven (not shown), and are then weighed in order to determine the fiber content of each sample. The system of the present invention provides a procedure for simultaneously analyzing multiple samples each contained in an individual bag, and dramatically improves the efficiency of fiber determination, and minimizes the investment in the equipment required for the analysis. The filter bag further eliminates the difficulties of filtration and permits the processing of multiple samples by maintaining the individual integrity of the sample and the bag during batch detergent refluxing and rinsing operations.

By contrast, the process currently being used in the field, as illustrated above in FIGS. 1A–1E, requires weighing out six (6) samples and boiling these samples in individual reflux containers as shown in the drawing. These samples are then transferred quantitatively to six (6) pre-tarred individual filter units and the filtering takes place under vacuum at separate stations for each sample. The remaining fiber is then hot water washed and solvent rinsed as illustrated in the drawings. The filter unit containing the fiber is then dried in an oven, and then weighed as in the procedure of the current invention.

The bags used in the present invention may comprise any suitable material having a porosity selected to allow for the removal of non-fiber components from the feedstuff while retaining the fiber components of said feedstuff within the bag. Suitable materials for the filter bag or member may comprise polyester, fiberglass, polyethylene, polypropylene or nylon. In general, the filter material should retain particles that have a maximum dimension size of at least about 5 microns to 40 microns and larger. In terms of porosity, bags suitable for use in the present invention typically have a range from about 5–40 microns. In one embodiment, a filtration grade spunbonded polyester was used for the bag material, this material is available from Snow Filtration Company of Cincinnati, OH under the REEWAY trademark, Style 2295.

Although the present invention has preferably been illustrated with the use of a sealed fabric bag, it should be understood that other filter members or devices could be used in the present invention. For example, a porous plastic or mead device in the form of a sealable container could be used in place of a fabric bag.

The material which may be analyzed by the present invention to determine fiber content includes human food or any suitable animal feed ingredient, which is hereinafter referred to as feedstuff. Typical food which may be analyzed for fiber content includes, without limitation, vegetables, grains and cereals. Typical feedstuff which may be analyzed for fiber content by the current invention include, without limitation, those falling under the general categories of forages, silages, grains and by-products. A more complete listing of suitable specific materials which may be analyzed for fiber content by the technique of the present invention is contained in a 1992 edition of the Table entitled *Analysis of Feed Ingredients, Ruminants of the Feed Industry Red Book*, pages 106-109 which is incorporated herein by reference.

The following example illustrates a preferred method of carrying out the present invention and for purposes of illustration uses the hardware illustrated in FIGS. 2A-2E and 3 of the drawings.

EXAMPLE

A 5 cm×5 cm polyester filter bag is first weighed. The surface of the bag functions as a three dimensional filtering membrane which retains particles of a size about 5 microns and larger. The bag is made of filtration grade spun bonded polyester available from Snow Filtration Company under the tradename Style 2295. The bag is then filled with 0.5 gm±0.01 gm sample of a selected feedstuff. The bag is then closed within about ⅛" of its open end by heat sealing (heat sealing of bag does not alter weight). A heat sealer of the type illustrated in FIG. 2B is available from Ankom Company of Fairport, NY under the tradename No. 1915 Heat Sealer. The sealed bag is positioned in the bag suspender of the type illustrated in FIG. 2C. The procedure is repeated for 11 additional samples. A 3 liter reaction kettle (See FIG. 3) containing 100 ml of neutral detergent solution per 0.5 gm sample is heated to 98° C.

|  | Neutral Detergent Solution |
| --- | --- |
| 540 gm | sodium lauryl sulfate |
| 335 gm | EDTA disodium salt |
| 122.6 gm | sodium borate |
| 82.1 gm | disodium hydrogen phosphate |
| 180 ml | triethylene glycol |

The bag suspender containing the 12 bags each containing a sample is inserted in the heated solution for 60 minutes while being mildly raised and lowered ⅛" at 60 cycles per minute by a mechanical agitator. The bag suspender is then removed from the heated detergent solution and placed directly into a 2L beaker of heated water (approximately 50 ml per bag). This hot water rinse is repeated until the water is nearly clear (3-5 rinses). The bags are then removed from the bag suspender and soaked 3-4 minutes in enough acetone to cover the bags. The bags are air dried then placed in an oven for at least 4 hours at 90-95 deg. Centigrade. They are then equilibrated to ambient temperature in a desiccator and weighed to determine the fiber content of each individual feedstuff sample.

When using the ADF analysis the following solution is used with the method described above for the NDF analysis.

|  | Acid Detergent Solution |
| --- | --- |
| 20 liters | 1N sulfuric acid |
| 400 gm | cetyl trimethylammonium bromide (CTAB) |

The objective of the present invention was to simplify and improve the efficiency of fiber analysis. As can be seen, the conventional filtering method has been replaced by a filter bag where each sample is placed in an individual bag and sealed closed. The isolation of samples in individual bags permits the incorporation of a number of bags in a single vessel during the detergent digestion and rinse operations.

A series of feed samples were analyzed using the filter bag technique of the present invention, described in the Example above, to determine the precision and accuracy of this technique. The results were compared with the NDF values determined by the standard procedure performed by Northeast Dairy Herd Improvement Association and The University of Wisconsin. The NDF results are summarized in the following table.

| FEED TYPE | CONVENTION PROCEDURE | | FILTER BAG PROCEDURE | |
| --- | --- | --- | --- | --- |
|  | NDF | SD | NDF | SD |
| Legume Hay | 42.50% | 1.40 | 42.66% | 1.02 |
| Alfalfa | 31.72% | .26 | 31.75% | .51 |
| Corn Silage | 58.27% | .63 | 58.17% | .30 |

A comparison of NDF values of the conventional procedure with the filter bag procedure of the present invention show almost identical results. The standard deviation (SD) is also comparable. This demonstrates the ability of the filter bag to allow digestion of feed components while retaining the fiber.

The forgoing examples and methods have been described in the specification for the purpose of illustration and not limitation. It should be understood that other modifications and ramifications of the present invention will occur to those skilled in the art based upon this disclosure and are intended to be within the scope of this invention.

What is claimed is:

1. A method for determining the fiber content of a feedstuff which comprises:
   (a) providing a sample of a feedstuff of a predetermined weight contained within a sealed container having a predetermined porosity;
   (b) exposing the container of (a) in a heated detergent containing solution for a time sufficient to remove substantially all of the soluble solids from said feedstuff while retaining the fiber components within said container;
   (c) removing said container from said detergent solution and rinsing said container in an aqueous solution to clean and remove any residual detergent solution from said container, followed by rinsing in an organic solvent and then drying; and
   (d) weighing said container to determine the fiber content of said feedstuff.

2. The method of claim 1 in which a plurality of containers are simultaneously treated by process steps (a)-(d).

3. The method of claim 1 in which the sample comprises a food.

4. A method of fiber analysis for feedstuffs which comprises:
   (a) providing a sample of feedstuff of a predetermined weight in a sealed fabric bag having a porosity selected to allow for the removal of the solubilized components of said feedstuff by solubilizng them in the detergent from said bag while retaining the fiber components of said feedstuff within said bag;
   (b) placing said bag in a heated detergent solution for a time sufficient to solubilize the non-fiber components of said feedstuff while retaining the fiber components within said bag;
   (c) rinsing said bag in an aqueous solution to remove residual detergent, followed by rinsing in an organic solvent and drying; and
   (d) weighing; said bag to determine the fiber content of said feedstuff.

5. The method of claim 4 in which a plurality of bags are simultaneously processed together.

6. The method of claim 5 in which the bags and/or solution is agitated during the heating process of step (b).

7. A method of fiber analysis for foods which comprises:
   (a) providing a sample of food of a predetermined weight in a sealed fabric bag having a porosity selected to allow for the removal of the solubilized components of said food by solubilizng them in the detergent from said bag while retaining the fiber components of said food within said bag;
   (b) placing said bag in a heated detergent solution for a time sufficient to solubilize the non-fiber components of said food while retaining the fiber components within said bag;
   (c) rinsing said bag in an aqueous solution to remove residual detergent, followed by rinsing in an organic solvent and drying; and
   (d) weighing said bag to determine the fiber content of said food.

8. The method of claim 7 in which a plurality of bags are simultaneously processed together.

9. The method of claim 8 in which the bags and/or solution is agitated during the heating process of step (b).

* * * * *